(12) United States Patent
Beaupre et al.

(10) Patent No.: US 9,199,391 B2
(45) Date of Patent: Dec. 1, 2015

(54) PROBE AND METHOD FOR OBTAINING RHEOLOGICAL PROPERTY VALUE

(75) Inventors: Denis Beaupre, Saint-Catherine-de-la-Jacques-Cartier (CA); Jerome Chapdelaine, Saint-Nicolas (CA); Frederic Chapdelaine, Saint-Nicolas (CA)

(73) Assignee: I.B.B. RHEOLOGIE INC., Sainte-Catherine-de-la-Jacques-Cartier (CA)

( * ) Notice: Subject to any disclaimer, the term of this patent is extended or adjusted under 35 U.S.C. 154(b) by 909 days.

(21) Appl. No.: 13/500,643

(22) PCT Filed: Oct. 7, 2010

(86) PCT No.: PCT/IB2010/054542
§ 371 (c)(1),
(2), (4) Date: Apr. 6, 2012

(87) PCT Pub. No.: WO2011/042880
PCT Pub. Date: Apr. 14, 2011

(65) Prior Publication Data
US 2012/0204625 A1    Aug. 16, 2012

Related U.S. Application Data

(60) Provisional application No. 61/249,321, filed on Oct. 7, 2009.

(51) Int. Cl.
*B28C 7/00* (2006.01)
*G01N 11/14* (2006.01)
*B28C 7/02* (2006.01)
*G01N 11/00* (2006.01)

(52) U.S. Cl.
CPC ............... *B28C 7/024* (2013.01); *G01N 11/14* (2013.01); *G01N 2011/0046* (2013.01); *G01N 2203/0676* (2013.01)

(58) Field of Classification Search
CPC ........... G01F 1/28; B28C 5/422; B28C 7/024; B28C 7/026; B28C 7/02; B28C 7/022; G01N 33/383; G01N 11/14; G01N 2011/0046; G01N 11/10; G01N 11/00; G01N 2203/0676; B01F 15/00246; B60P 3/16
USPC ............ 73/54.31, 54.01, 54.02, 54.03, 54.23, 73/54.28, 54.32, 54.37, 54.38, 861.71; 366/142
See application file for complete search history.

(56) References Cited

U.S. PATENT DOCUMENTS

| | | | | |
|---|---|---|---|---|
| 3,688,588 | A * | 9/1972 | Hill | ................................ 73/451 |
| 4,356,723 | A | 11/1982 | Fay | |
| 5,541,855 | A | 7/1996 | Enzler | |
| 6,227,039 | B1 | 5/2001 | Te'eni | |
| 2007/0295104 | A1 * | 12/2007 | Ellegood | .................... 73/861.79 |

FOREIGN PATENT DOCUMENTS

| | | |
|---|---|---|
| CA | 2555628 A1 | 9/2005 |
| CA | 2725887 | 12/2009 |
| EP | 0 308 966 A3 | 5/1990 |
| EP | 0 924 020 A1 | 6/1999 |
| EP | 1961538 A2 | 8/2008 |
| WO | 2007/060272 A2 | 5/2007 |
| WO | WO2011042880 A1 | 4/2011 |

* cited by examiner

*Primary Examiner* — Daniel S Larkin
*Assistant Examiner* — Jamar Ray
(74) *Attorney, Agent, or Firm* — GrayRobinson, P.A.

(57) ABSTRACT

The probe can include a base and a resistance member extending from the base and onto which a resistance pressure is imparted by a rheological substance when the resistance member is submerged and moved therein. Rheological properties can be obtained using values indicative of the resistance pressure both in a low speed range and in a high speed range.

9 Claims, 10 Drawing Sheets

Calib with original hole position (high-sensitivity)

| Mass(kg) | P (kPa) | Voltage (V) |
|---|---|---|
| 5.6 | 12.62 | -0.35 |
| 8.2 | 18.47 | -0.57 |
| 3.8 | 8.56 | -0.2 |
| 0 | 0 | 0.14 |
| 3.2 | 7.21 | -0.14 |

' # PROBE AND METHOD FOR OBTAINING RHEOLOGICAL PROPERTY VALUE

CROSS-REFERENCE TO RELATED APPLICATIONS/PRIORITY CLAIM

This application claims priority of U.S. Provisional application No. 61/249,321 filed Oct. 7, 2009 by applicants, the contents of which are hereby incorporated.

BACKGROUND

Rheology is the study of the flow of matter. This application more specifically addresses the flow of soft solids which exhibit fluid-like behaviors. Many applications can benefit from or even require the measurement of rheological properties of substances, particularly in cases where such properties change over time.

Concrete is a good example, for once mixed, concrete is typically continuously mixed in a mixer, which are sometimes mounted on trucks, to extend its life prior to solidification. However, even though mixers extend the life of mixed concrete, it does not make it last indefinitely, and the rheological properties of concrete in the mixer such as viscosity and yield can vary over time. For this reason, a common testing method referred to as the slump test is commonly used to monitor the "workability" of the concrete prior to application. The slump test involves removing concrete from the mixer, placing it in a truncated cone of a given height, removing the cone, waiting for the concrete to stabilize, and measuring the distance the concrete has slumped down.

In the food industry to give another example, some rheological properties can vary during cooking or other chemical reactions, and monitoring rheological properties can provide indicia that a given step in the process has been completed.

There are modern methods of obtaining rheological properties, but each had particular limitations. There remained room for improvement

SUMMARY

Considering one aspect, providing a stand-alone instrument which can be referred to as a probe, which has both means of monitoring the resistance to movement or pressure exerted thereon by the substance to characterize, and means of monitoring the movement speed of the probe relative the substance, from which rheological properties such as yield and viscosity can be calculated, can provide a significant advantage, especially when used on a wall of a revolving container for instance, where external communication with other units poses challenges.

Henceforth, in accordance with one aspect, there is provided a rheological probe unit for use in a cylindrical container rotatable about its axis and containing a substance having rheological properties, the rheological probe unit comprising: a base mountable in a wall of the cylindrical container; a resistance member extending from the base in a radial orientation when the base is mounted to the cylindrical container, and onto which a resistance pressure is imparted by the rheological substance when the resistance member is submerged and moved therein by the rotation of the cylindrical container; a force sensor adapted to provide force values indicative of the resistance pressure at given points in time; a speed sensor adapted to provide speed values indicative of the speed at which the resistance member is moved in the substance at given points in time, in both a low speed range and a high speed range; a power source; and an emitter.

Considering another aspect, the measurement of the resistance to movement exerted by the substance to characterize posed particular challenges which remained to be addressed. Henceforth, in accordance with another aspect, there is provided: a rheological probe for use in obtaining at least one value indicative of a rheological property of a substance in which the rheological probe is to be immersed and relative to which the rheological probe is to be transversally moved, the rheological probe unit comprising: a base; an inner member fixedly connected to the base and extending away therefrom, the inner member having in succession base portion proximate the base, a deformation portion located away from the base, and a tip; a shell member covering the inner member from the tip and downwardly along the deformation portion and base portion, the shell member being pivotable about an axis extending across the base portion when subjected to a resistance pressure imparted by the relative movement in the rheological substance, and being connected to the tip to transfer a force resulting from the resistance pressure and thereby elastically deform the deformation portion; and a deformation sensor mounted to the deformation portion for providing a value indicative of the resistance pressure.

Also, in accordance with still another aspect, there is provided a probe for determining at least one rheological property of a fluid contained in a recipient, the probe comprising: an inner member holding a load cell; an outer member adapted to be placed in contact with said fluid, said outer member being submittable to a pressure applied by the fluid and being adapted to transfer a force resulting from said pressure to the inner member and thereby deform the load cell, the load cell thence providing an indication of a value of said deformation; a base connected to the inner member, said load cell being prevented from being in contact with said fluid by said outer member and said base; at least one position sensor to provide an indication of a position of the probe; an electronic module in electronic communication with the load cell and the at least one position sensor, the electronic module having a processing unit to determine a speed value of the probe based on said indication of a position and to determine the at least one rheological property of the fluid based on the speed value of the probe and the value of the deformation obtained from the load cell; wherein said at least one rheological property of the fluid is determined when the probe is displaced in the fluid in the recipient and without having to remove a sample of fluid from the recipient to analyze it externally.

In accordance with another aspect, there is provided a method for determining at least one rheological property of a fluid contained in a recipient, the method comprising: providing an indication of a position value of the probe using at least one position sensor; sensing a deformation of an outer member of a probe resulting from a force applied by the fluid on the probe and providing an indication of a value of said deformation; determining a value of the force applied to the probe when in contact with said fluid in said recipient using said value of said deformation; determining a speed value of the probe using the determined position value; and determining the at least one rheological property of the fluid based on said speed value of the probe and the value of the force applied on the probe; wherein said at least one rheological property of the fluid is determined when the probe is displaced in the fluid in the recipient and without having to remove a sample of fluid from the recipient to analyze it externally.

In accordance with still another aspect, there is provided a probe adapted to move with a mixer for determining at least one rheological property of a fluid, the probe comprising: an outer member being deformable when submitted to a force applied by the fluid, the outer member comprising: an inner member connected to the base for holding a load cell in condition to be deformed; a load cell having a first end connected to the inner member and a second end connected to the outer member for sensing the force applied by the fluid on the outer member and being deformed by the force and determining a value of the force, the load cell being deformed proportionally to the deformation of the outer member; and a base connected to the outer member and the inner member, the base being adapted to be mounted on an interior wall of the mixer, the base comprising: an electronic module in electronic communication with the load cell, the electronic module having at least one position sensor placed on an axis parallel to a mixer radius vector to determine a position value of the probe and a processing unit to determine a speed value of the probe, the processing unit determining the at least one rheological property of the fluid based on the speed value of the probe and the value of the force obtained from the load cell when the probe is in operation in the mixer without having to remove a sample of fluid from the mixer and analyze it externally, the processing unit synchronizing the force applied by the fluid on the outer member with the position value to determine the speed value.

In accordance with a further aspect, there is provided a probe adapted to move with a mixer for determining at least one rheological property of a fluid, the probe comprising: an outer member being deformable when submitted to a force applied by the fluid, the outer member comprising: an inner member connected to the base for holding a load cell in condition to be deformed; a load cell having a first end connected to the inner member and a second end connected to the outer member for sensing the force applied by the fluid on the outer member and being deformed by the force and determining a value of the force, the load cell being deformed proportionally to the deformation of the outer member; and a base connected to the outer member and the inner member, the base being adapted to be mounted on an interior wall of the mixer, the base comprising: an electronic module in electronic communication with the load cell, the electronic module having at least one accelerometer to determine a position value of the probe and a processing unit to determine a speed value of the probe, the processing unit determining the at least one rheological property of the fluid based on the speed value of the probe and the value of the force obtained from the load cell when the probe is in operation in the mixer without having to remove a sample of fluid from the mixer and analyze it externally.

In accordance with another aspect, there is provided a method for determining at least one rheological property of a fluid in a mixer, the method comprising: determining a position value of the probe using at one accelerometer; detecting a deformation of an outer member of a probe resulting from a force applied by the fluid on the probe; determining a value of the force applied to the probe when in operation in the mixer; determining a speed value of the probe moving with the mixer using the determined position value; and determining the at least one rheological property of the fluid based on a speed values of the probe and the value of the force applied on the probe when in operation in the mixer without having to remove a sample of fluid from the mixer and analyze it externally.

DESCRIPTION OF THE DRAWINGS

Further features and advantages of the present invention will become apparent from the following description in conjunction with the appended drawings, in which.

It will be noted that throughout the appended drawings, like features are identified by like reference numerals.

DETAILED DESCRIPTION

Figure 1:
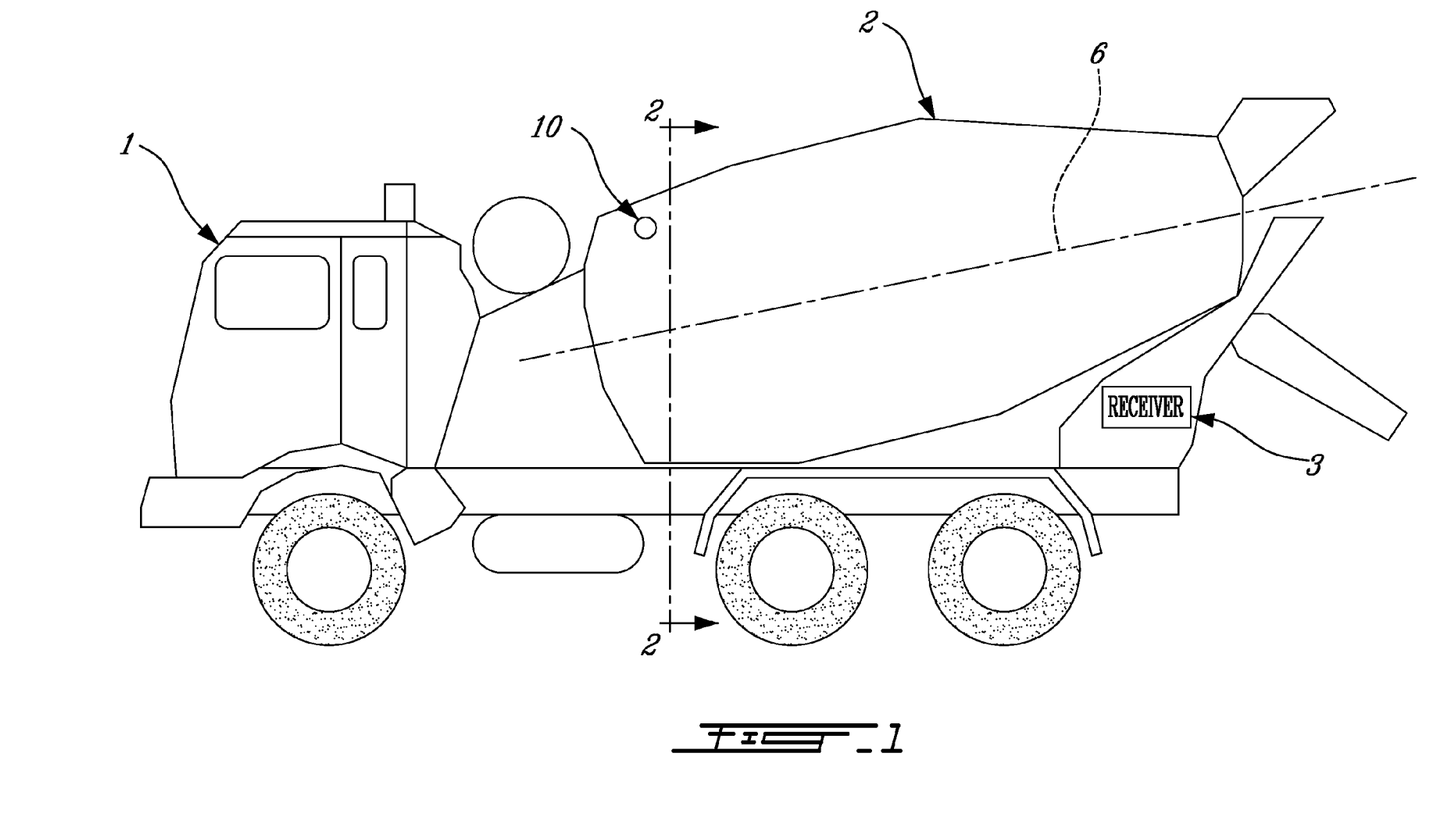
FIG. 1 is a schematical side view of a mixing truck.

Reference is made to FIG. 1, which is provided to provide context of one example of a possible application of a probe, that is to obtain rheological properties of concrete inside the mixer 2 of a mixing truck. FIG. 1 shows a side view of a truck, with probe 10 schematically shown in the mixer 2 to obtain indications of rheological properties. It can further obtain indications of mixer speed and direction, fluid flow properties, fluid temperature for instance, as will be detailed below. Because there is a challenge in bringing a wired connection inside a rotary container, the probe can transmit data to a receiver 3 via a wireless connection and be self-powered. In a mixing truck, the rotation axis 6 of the mixer is strongly inclined relative to the vertical.

Following this example, reference will be made to concrete as being the substance to rheologically characterize; but it is understood that the probe can be used with another container or recipient than a mixer 2, rotary or not, which may contain other substances exhibiting rheological properties such as fluids for the food processing industry, the paint industry, the oil industry, etc. Similarly mixers are not necessarily provided on trucks and other types of mixers can be used. For example, the mixer can be an industrial mixer, a blending system including high shear mixers, in-line mixers, or agitators.

Figure 2:
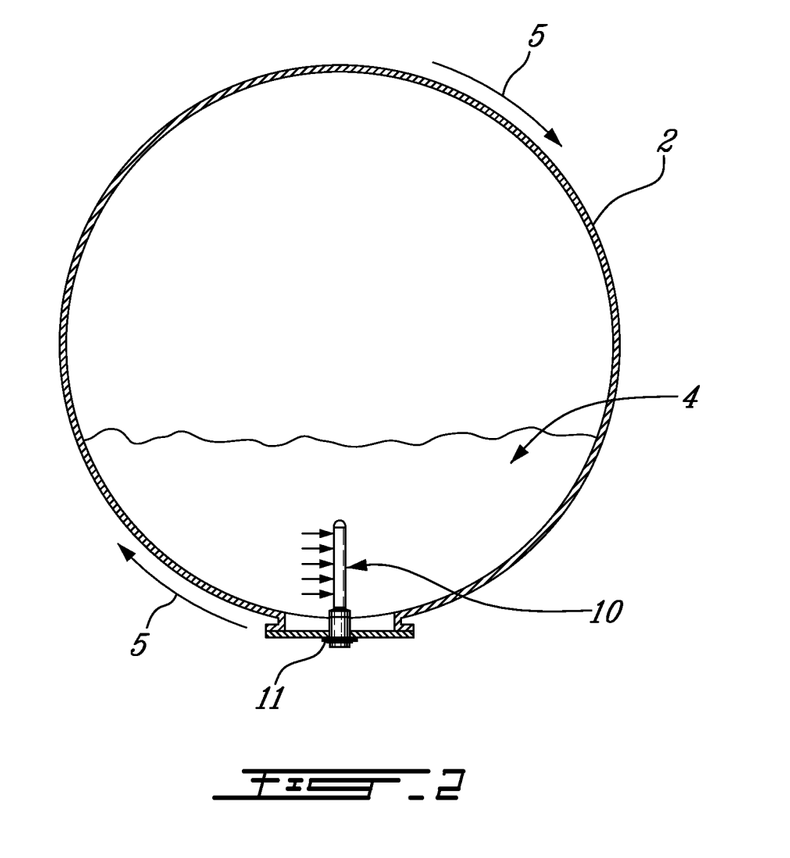
FIG. 2 is a schematical cross-section view of the mixer of FIG. 1 taken along cross-section lines 2-2 showing an example of a probe.

Reference is now made to FIG. 2, showing an example of a probe 10. In this example, the probe 10 has a base 11, which is affixed to the interior wall of the mixer 2. In the case of a mixing truck, for instance, the probe 10 can be mounted in the inspection door of the mixer 2 and the base can have an openable bottom exposed outside the container for operations such as maintenance. During use, the probe 10 rotates with the mixer 2 in the rotating direction shown by arrows 5, or in the opposite direction, depending of whether the mixer is mixing or emptying the load, for instance. In both cases, the concrete remains toward the bottom of the container due to the action of gravity and its limited viscosity. The probe 10 is thus immersed into the concrete at each revolution and travels therein. The concrete exerts a resistance pressure shown schematically with arrows opposing the movement of the probe 10. The probe 10 can directly measure parameters such as the position of the probe, the force (or resistance pressure exerted by the substance on the probe), the temperature, etc. The probe 10 can subsequently use these parameters to determine the speed, and thence use speed and force values for instance to obtain an indication of properties of the fluid such as the viscosity, the yield, the cohesion, etc. The probe 10 can be made of any suitable material given the potentially harsh environment.

In another embodiment, for example, the recipient can be fixed and a probe can be moved manually, be provided on rails or have other movement means over the recipient where the movement means can be used to displace the probe at speeds which can optionally be controlled.

Figure 3:
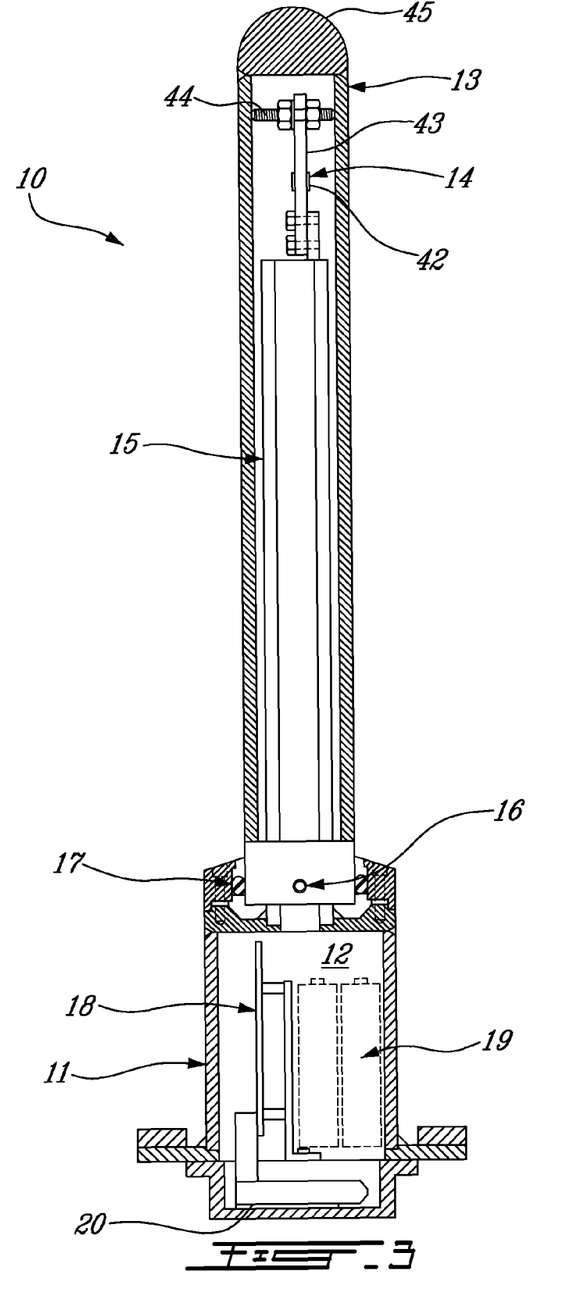
FIG. 3 is a longitudinal cross-sectional view of the probe of FIG. 2.

Reference is now made to FIG. 3, which is a longitudinal cross-sectional view of an example of a probe 10. The base 11 includes plates that can be adapted to be mounted to the wall of the mixer 2, from the inside or the outside of the mixer, for example using a hole perforated in the plate(s) and/or the mixer wall.

The base 11 extends perpendicularly into the mixer 2 and provides a hollow cavity 12 that can contain and protect an electronic module 18, a power supply 19, and a transmitter 20 to transmit data from the probe 10 to the receiver 3.

The electronic module 18 can be powered with replaceable or rechargeable batteries for instance. In one embodiment, the electronic module 18 can use various algorithms to reduce its power requirements, and thus maintenance, such as turning off the radio transmitter between transmissions, reducing its processing speed when the mixer 2 does not rotate, etc. In another embodiment, the batteries can be rechargeable and combined with one or more other power sources such as solar panels, or inductive loops to further reduce maintenance.

The probe 10 comprises an inner member 15, which is connected to the base 11 and extends into the mixer 2. The inner member 15 can be connected with the base using bolts or screws. The inner member 15 can also be attached to the base 11 and maintained in place with a seal 17.

The probe 10 comprises an outer member 13 which received the resistance pressure from the substance. The outer member 13 comprises a hollow interior that allows the outer member 13 to cover a load cell 14 and the inner member 15 of the base 11. The outer member 13 is affixed to the base 11 with a pivot hinge 16. The pivot hinge 16 maintains in place the outer member 13 with the base 11 and allows the top part of the outer member 13 to slightly move from left to right when the probe 10 is in operation in the mixer 2. The movement of the outer member due to the pressure exerted by the substance is transmitted to a deformation portion of the inner member via a connection 44 (in this case an abutment connection by abutment against the end of a bolt). The deformation of the deformation portion 43 (in this case a metal plate) will be sensed by the load cell 14 applied thereon, which can include one or more strain gauges 42 for instance. A cap 45 is added at the end of the outer member 13.

In one embodiment the outer member 13, the inner member 15 and the base 11 can be cylindrical. However, it is understood that the outer member 13, and the base 11 can alternately have a rectangular, a hexagonal, an ovoid shape, or any other shape. It will be understood that the shape of these members which are in contact with the mixture will affect the resistance of the probe 10 into the mixture.

In another embodiment, the inner member 15 can have a rectangular, a hexagonal, an ovoid shape, or any other shape. It is understood that the shape of the inner member will typically not affect on the operation of the probe.

The height of the resistance member, or more particularly the outer shell in the above embodiment, can be selected as a function of the properties of the substance to characterize. Typically, soft solids reach a relative uniformity within a characteristics scale which is in function of the largest aggregates expectable in the substance. In the case of concrete for instance, the characteristic scale is in the order of the decimeter. Henceforth, the length or height of the resistance member was selected to be within this order of magnitude, whereas in an alternate embodiment for analysis of another substance having a different characteristic scale, the length or height of the resistance member can be adapted as a function of the characteristic scale.

In the particular embodiment depicted, for the sake of providing a truly full description, the probe can have a total height of 40 cm (or 4 dm) for instance, in which case the outer member can be 30 cm (or 3 dm) with a radius of 3.5 cm and the base 11 have an external radius of 4.5 cm for the purpose of giving a full example. One feature which affects the amount pressure applied to the outer member or shell is the surface area thereof. Henceforth, for example, in an alternate embodiment where the resistance member is wider, it can be selected to be shorter for instance. When in use into the mixer 2, the base can be affixed with together with a plate having of about 6 cm to the interior wall of the mixer 2.

Figure 4:
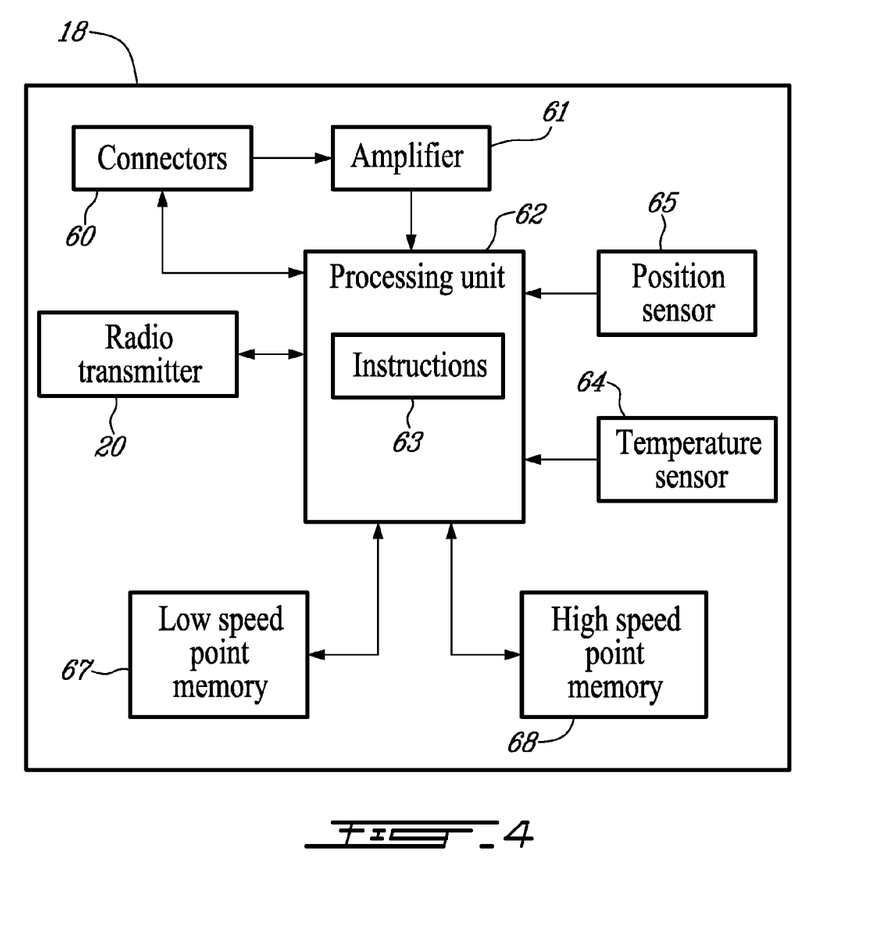
FIG. 4 is a block diagram representation of the probe of FIG. 2.

Reference is now made to FIG. 4, which is a schematic diagram of an example of an electronic module 18 of a probe 10. In this example, the electronic module 18 comprises an electrical amplifier 61. The electrical variation of the strain gauge 42 is of the order of a few millivolts and can thus require amplification by the amplifier 61 before it can be used. The electrical amplifier 61 amplifies the electrical variation detected by strain gauge 42. The electrical variation is then processed by the processing unit 62 to obtain an indication of the pressure or force that was initially applied by the fluid on the outer member 13. The processing unit 62 comprises instructions 63 of an algorithm. The instructions are executed by the processing unit 62 to determine rheological properties of the fluid. The processing unit 62 comprises software and hardware parts to execute different algorithms to process parameters measured by the probe 10.

The electronic module 18 may comprise a plurality of sensors such as position sensors and temperature sensors. FIG. 4 shows a position sensor 65 and a temperature sensor 64. The probe can have memory such as a low speed point memory 67, a high speed point memory 68 for storing measurements made by the plurality of sensors of the probe 10.

The temperature sensor 64 measures the temperature inside the probe 10. When the probe 10 is moving through the fluid, after a stabilization delay, the temperature inside the probe 10 stabilizes to the fluid temperature. Hence, the temperature sensor 64 measures the fluid temperature. The probe 10 may use a Negative Temperature Coefficient (NTC) resistor, which is also called a thermistor. In another embodiment, other types of sensors can be used are such as Resistance Temperature Detectors (RTDs), semiconductors temperature sensors, etc.

The fluid temperature can be used as an information for quality production control at a batching plant. For example, ice can be added to maintain concrete in a concrete mixer truck embodiment at a certain temperature. In this case, the temperature sensor 64 is used as a feedback for the concrete temperature. The temperature sensor can continuously measure and provide the concrete temperature to determine the amount of ice to be added to the concrete mixture.

The position sensor 65 can include a micro-electro-mechanical system (MEMS) accelerometer for instance. The accelerometer can be placed with is axis oriented toward the axis of the mixer for instance and henceforth be affected by centripetal acceleration and earth gravity acceleration to obtain signal indicative of angular position. In this example, the processing unit 62 combines the angular position readings with a chronometer or timer to determine the probe rotation speed. The processing unit 62 synchronizes the load cell reading with an angular position sensor to systematically interpret measurements from the probe 10, when the probe 10 is in operation and at the bottommost point of its rotation into the mixture of the mixer 2.

Taking the measurements at the bottommost point of the rotation of the mixer 2 ensures that the probe is located in the mixture when acquiring the data. Using the accelerometers can allow to determine the bottommost point.

Alternatively, the processing unit 62 can determine that the probe 10 is in the mixture by continuously measuring the force applied on the outer member 13. When the force increases substantially, it means that the probe 10 is located in the fluid and when the force decreases substantially, it means that the probe is exiting the mixture. Thus, it can then be easier to remove a noise component from the force signal as the noise would be somewhat constant. This can also allow the determination of the level of the fluid and thus by calculation, the amount of fluid in the mixer.

Interestingly, a rough rotation speed can be estimated without a position sensor simply by timing the delay between two subsequent substantial increases or decreases in force, which gives an indication of the time it takes for the drum to make a complete revolution. If the information concerning the path of the probe is available (typically linked to the diameter of the truck), the length of the path can be divided by the time to give a rough average speed approximation. Such processing by the processing unit can thus constitute a speed sensor which can replace computation of position data if desired.

Also, obtaining the information of the position at which the probe enters and exits the substance by detection for instance of sudden increase and sudden decrease in force value, can allow, given the geometry of the container is available, to calculate a value indicative of the volume of the substance in the container.

Similarly, the determination of the presence of the probe 10 in the mixture can be made, for example, with the temperature detected by the temperature sensor. When the temperature increases substantially, the probe 10 is determined to be in the mixture and when the temperature decreases substantially, the probe 10 is determined to have exited the fluid or vice-versa, depending on the qualities of the fluid being mixed.

By using the force value or the temperature value, the processing unit 62 is able to determine if the probe is in the fluid without knowing the amount of mixture in the mixer 2 and the determination is therefore independent of the amount of mixture in the mixer 2.

Alternately, if using a position sensor, the identification of the position of entry of the probe and the position of exit can be correlated to a volume of concrete in the mixer.

In one embodiment, any sensor that is able to produce a signal indicative of a position reference for the probe 10 can be used, such as an accelerometer, an inductive non-contact position sensor, a string potentiometer, a linear variable differential transformer, a potentiometer, a capacitive transducer, an eddy-current sensor, a Hall effect sensor, a grating sensor, a rotary encoder, a seismic displacement pick-up module, a piezo-electric transducer, a photodiode array, etc.

Then the processing unit 62 can use an internal chronometer to measure the time elapsed between each known position encounter. The speed can be determined, and the absolute position of the mixer 2 at any given time can be interpolated.

In another embodiment, a magnetic sensor can be used as reference. In this case, a magnet (or many magnets) is affixed to the truck frame at a known position. A magnetic sensor in the probe 10 detects when the probe 10 moves near the magnet. In an alternate embodiment a reflective optical sensor can also be used. In this embodiment, a reflective surface is affixed to the truck frame and the probe is equipped with a light emitter and receiver. When the probe 10 moves near the reflective surface, the emitted light is reflected back to the light receiver and a determination of the position of the probe can be made. In yet another embodiment, a sensor ball is confined in a cylinder having a first and a second end. The cylinder may contain a liquid or gas in which the sensor ball travels. Each time the sensor ball travels from the first end to the second end of the cylinder and vice versa, one can deduct that the probe is positioned in a certain direction. Once the ball has traveled one way and back, this indicates that a complete revolution of the mixer 2 was made. The processing unit 62 can also use a chronometer to measure the time elapsed between each revolution and thus can determine the speed of the probe 10. This is to give some examples.

Figure 5:
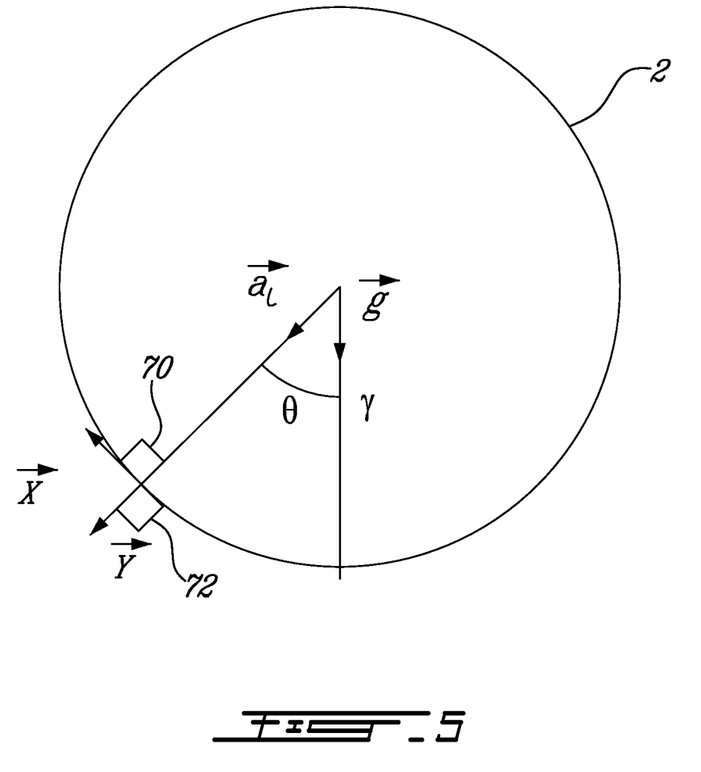
FIG. 5 is a schematic diagram of vectors used to determine speed values of a probe in accordance with an embodiment.

Reference is now made to FIG. 5, which is a schematic diagram of vectors of accelerometers used to determine speed values of the probe 10 in accordance with an embodiment. In FIG. 4, two MEMS accelerometers 70, 72 are used, but it is understood that more than two MEMS can be used to determine speed values of the probe. The readings of accelerometers 70, 72 are typically the vector dot product of the orientation vector of the accelerometers 70, 72 and the total acceleration vector. For example, in FIG. 4, The accelerometer 70 is oriented in the x axis direction while the accelerometer is oriented in the y axis direction. Each accelerometer orientation vector has a unit length, and the gravitational acceleration is normalized to 1G (where G is the gravitational acceleration). The accelerometer will respond to both gravity and any other acceleration such as centripetal acceleration and linear accelerations.

In one embodiment, a single accelerometer can be sufficient to determine the probe angle relative to earth but the sign of the angle is unknown. In this case, it would be possible to know that the probe 10 is at the bottom of the mixer 2 to take the fluid measurement, but the direction of the rotation would be unknown. However, using the accelerometers 70, 72 with a 90 degrees angle between them can provide the direction of the rotation. More particularly, the second accelerometer (oriented circumferentially) can provide this information and thus be used to determine rotation direction of the mixer if desired.

In the case of an industrial mixer in which the axis of rotation can be substantially vertical, a single accelerometer can be used to provide the speed. Indeed, the mathematical integration of the acceleration provides the speed and the change of direction of the probe.

The details of an exemplary calculation using the accelerometers is now provided in greater detail:

The accelerometer labeled x is in a radial orientation (pointing away from the mixer circle), the accelerometer labeled y other is in a tangent orientation. Assuming a constant rotation speed, the only acceleration involved are the earth gravitational acceleration (normalized so that $|\vec{g}|=1$ and the centripetal acceleration. The x and y analog readings given by the accelerometer can be as follows:

$$x = \vec{x} \cdot \left( \vec{g} + \frac{\vec{a}_c}{G} \right) = \vec{x} \cdot \vec{g} + \vec{x} \cdot \frac{\vec{a}_c}{G} = \vec{x} \cdot \vec{g} \quad (1)$$

$$y = \vec{y} \cdot \left(\vec{g} + \frac{\vec{a}_c}{G}\right) = \vec{y} \cdot \vec{g} + \vec{y} \cdot \frac{\vec{a}_c}{G} \quad (2)$$

where:
x=is the position of an accelerometer,
$\vec{x}$=the vector for the accelerometer,
y=is the position of an accelerometer,
$\vec{y}$=the vector of the orientation for the accelerometer,
G=gravitational acceleration,
$\vec{g}$=the vector for the gravitational acceleration,
$\vec{a}_c$=the vector for the centripetal acceleration.

Because $\vec{x}$ is perpendicular to $\vec{a}_c$, the accelerometer positioned at x is not affected by the centripetal position. The equations (1) and (2) can then be written as a function of the angle θ to give:

$$x = |\vec{x}||\vec{g}|\cos\left(\theta + \frac{\pi}{2}\right) = -\sin(\theta) \quad (3)$$

$$y = |\vec{y}||\vec{g}|\cos(\theta) + |\vec{y}|\frac{|\vec{a}_c|}{G}\cos(\theta) = \cos(\theta) + \frac{|\vec{a}_c|}{G} \quad (4)$$

Given that in (3) and (4), the angle θ can be solved, only if $|\vec{a}_c|$ is known, but the value depends on the angular rotation speed and the mixer radius. Those values are unknown yet. However, if it is assumed that $|\vec{a}_c|$<G, then when x=0, θ=0 or π. In which case:

$$y = \pm 1 + \frac{|\vec{a}_c|}{G} = \pm 1 + K \quad (5)$$

$$\frac{|\vec{a}_c|}{G} = K = \begin{cases} y - 1, & \text{when } y > 0 \\ y + 1, & \text{when } y < 0 \end{cases} \quad (6)$$

Thus, the offset is caused by the centripetal acceleration can be determined at the minimum twice on each rotation, when $|\vec{x}|=0$. That event can be easily detected in software by monitoring the sign change of x.

A similar algorithm could be made for $$\theta = \frac{\pi}{2} \text{ or } \frac{3\pi}{2}$$

but this would imply detecting when $|\vec{x}|=1$ which is difficult when any noise or offset is present in the signal.

The rotational speed can be calculated, both in angular notation ω in rad/sec, or in revolutions per minute (RPM) by either monitoring the time elapsed between each revolution (when θ crosses zero and checking before/after value to determine the rotation direction), or by continuously computing $$\omega = \frac{\partial \theta}{\partial t}.$$

From equations 1 to 6 and the constant K, it is possible to obtain an equation for r the radius of the mixer 2:

$$K = \frac{|\vec{a}_c|}{G} = \frac{\omega r^2}{G} \quad (7)$$

$$r = \sqrt{\frac{KG}{\omega}} \quad (8)$$

From equation 8, r radius of the mixer 2 can be deduced and v the linear speed at the center of the probe 10 can be obtained.

$$r' = r - \frac{l}{2} \quad (9)$$

$$v = \omega r' \quad (10)$$

Where l=length of the probe in meters.

For example, the following parameters can be determined with equations 7 to 10: the mixer instantaneous position, rotation speed in revolutions per minute (rpm), the mixer rotation direction (mixing or unloading), the mixer dimension, which can be determined from the centripetal acceleration and the angular speed, the probe linear speed, etc.

As described, the load cell 14 measures the force applied to the outer member 13. For a given fluid mixture, that force increases generally linearly with the speed. Because the total force depends on the outer member dimensions and shape, it is preferable to measure the average pressure applied by the fluid. To avoid having a result that depends on the mixer size, the probe linear speed is used. Then, the parameters of the probe 10 in operation in the fluid can be determined by a proportional relation between a pressure P and the linear speed v.

The linear speed v and the pressure are then simultaneously obtained by the electronic module 18. The load cell 14 gives a reading proportional to the force. The equation to calibrate the load cell 10 to give an equivalent pressure P is obtained as described below.

The torque T by a single force F applied at distance d from a rotation axis is:

$$T = Fd \quad (11)$$

If the force is generated by a pressure, for a small area, the force F can be derived with dF=P dA. Then by integrating dF=P dA, the torque T can be determined by a pressure on a finite plane with effective width of W and length of L is given by:

$$T = \int_0^L PWx\,dx = \frac{PWL^2}{2} \quad (12)$$

To calibrate the probe, it is thus possible to suspend a calibration mass 80 from the probe when oriented horizontally. Since the strain gauge 42 will give an analog reading proportional to the force applied to the probe 10, a calibration is required to retrieve the pressure. The calibration mass 80 is attached at a distance d from the rotation axis defined by the base 11. The torque T applied by the calibration mass 80 is:

$$T = Fd = mGd \quad (13)$$

When the equations (12) and (13) are combined together, the pressure is obtained with the following:

$$P = \frac{2mG}{LW} = \frac{2F}{LW} \quad (14)$$

where:
P=pressure in kPa,
m=mass in kg,
G=gravity (9.8 m/s$^2$),
L=probe length,
W=probe effective width,
d=distance of calibration mass from the rotation axis.

Figure 6A:
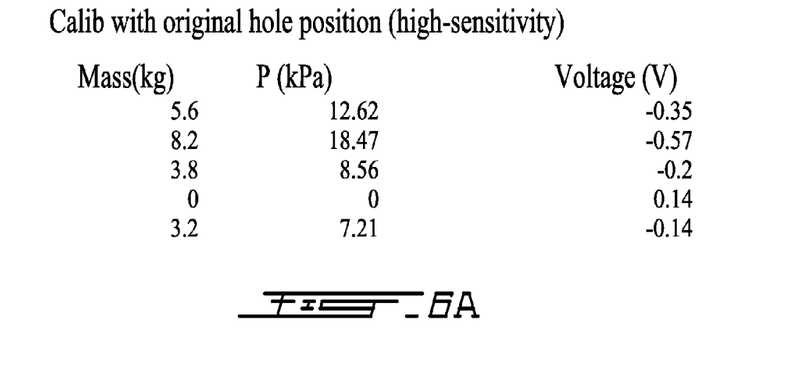
FIGS. 6A and 6B are graphical representations of calibration data.
Figure 6B:
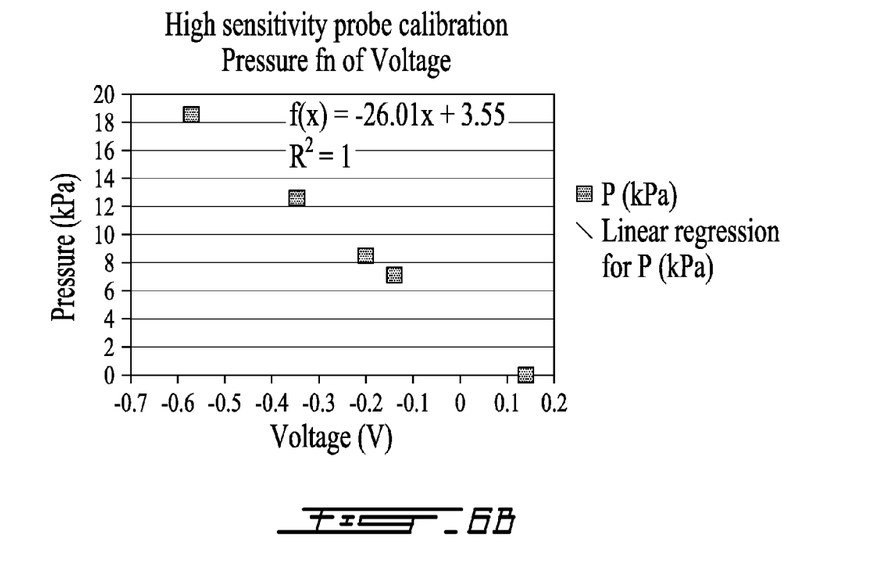

Reference is now made to FIG. 6A, which is an example of a table of values obtained during a calibration of the load cell 14 in accordance with an embodiment. Equation (14) can be used to build the calibration curve by applying many known masses, measuring the electrical variation and determining the pressure, given the known masses. In FIG. 6B, the values of the table of FIG. 6A are shown in a graphical representation of speed versus pressure. In FIG. 6B, the pressure (in kPa) is determined using the electrical variation of the probe 10 (in voltage).

Figure 7:
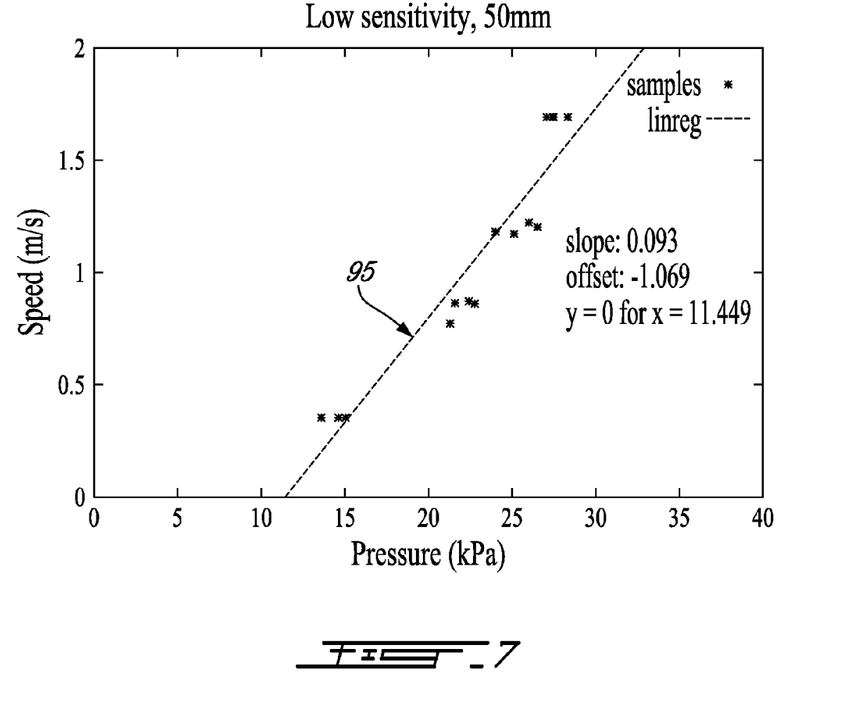
FIG. 7 is a graphical representation of speed versus pressure values obtained during operation of a probe in accordance with FIG. 2.

Reference is now made to FIG. 7, which is a graphical representation of the speed versus pressure values obtained during the operation of the probe 10 in concrete at different speed settings and over a limited period of time. The pressure applied on the probe by the fluid was determined at different values of speed. More particularly, there should be at least one value of pressure (or the equivalent force), and preferably at least three, obtained at a low speed range, and at least one value of pressure (or the equivalent force), and preferably at least three, obtained in a high speed range. Using these values, allows to plot an extrapolated rheological curve, which can be done by the electronic module 18 for instance. In an alternate embodiment, the probe can emit these values and an electronic module for extrapolating the rheological curve using these values can be provided externally, in conjunction with a receiver, for instance. When approximating the curve going through all determined points by a straight line 95 properties of the mixture such as, for example, the viscosity and the yield of the fluid can be extracted.

The viscosity can be determined using the slope of the straight line 95 passing through the points (or 1/slope of the graph of FIG. 7).

The yield can be determined as well by extrapolating the pressure at zero speed $\tau_0$ using the straight line 95.

The probe 10 determines the viscosity and yield by continuously monitoring the probe speed and automatically performing a two point test when the probe is at the bottommost point of its rotation in the fluid. The probe 10 determines properties of the fluid and properties concerning the mixer 2 using multiple ranges of speed. For example, the probe can determine properties for the fluid using a low speed window and a high speed window. This allows a realistic curve to be plotted. For example, in the case of concrete in an average mixer truck, the low speed window may comprise speeds between 0.25 and 0.75 m/s and the high speed window may comprise speeds between 1.5 and 2 m/s. It will be noted that the speed windows can greatly vary depending of applications.

The probe 10 continuously monitors speed values and determines pressure values each time the probe 10 is in operation into the mixture of the mixer 2. If the current speed is inside the low speed window, the pressure and speed are stored in the low speed point memory 67. If the speed in inside the high speed window, the pressure and speed are stored in the high speed point memory 68. Each time a new high speed point is measured, the processing unit 62 determines a straight line that passes through the high and low speed points and determines the viscosity and yield. Each time a low speed point is measured, the processing unit 62 determines the yield using the previously determined viscosity. A proper calibration of the probe 10 using different compositions of fluid, a lookup table or a curve fitting equation can be built to determine the slump from the yield. With time, the rheological equation will change. The points in the lower speed range will tend to change more rapidly, and should be re-taken more frequently than the points in the higher speed range.

The slump can be evaluated by:

$$\text{Slump} = k\tau_0 \quad (15)$$

where:
k=constant,
$\tau_0$=pressure at a zero speed.

Figure 8:
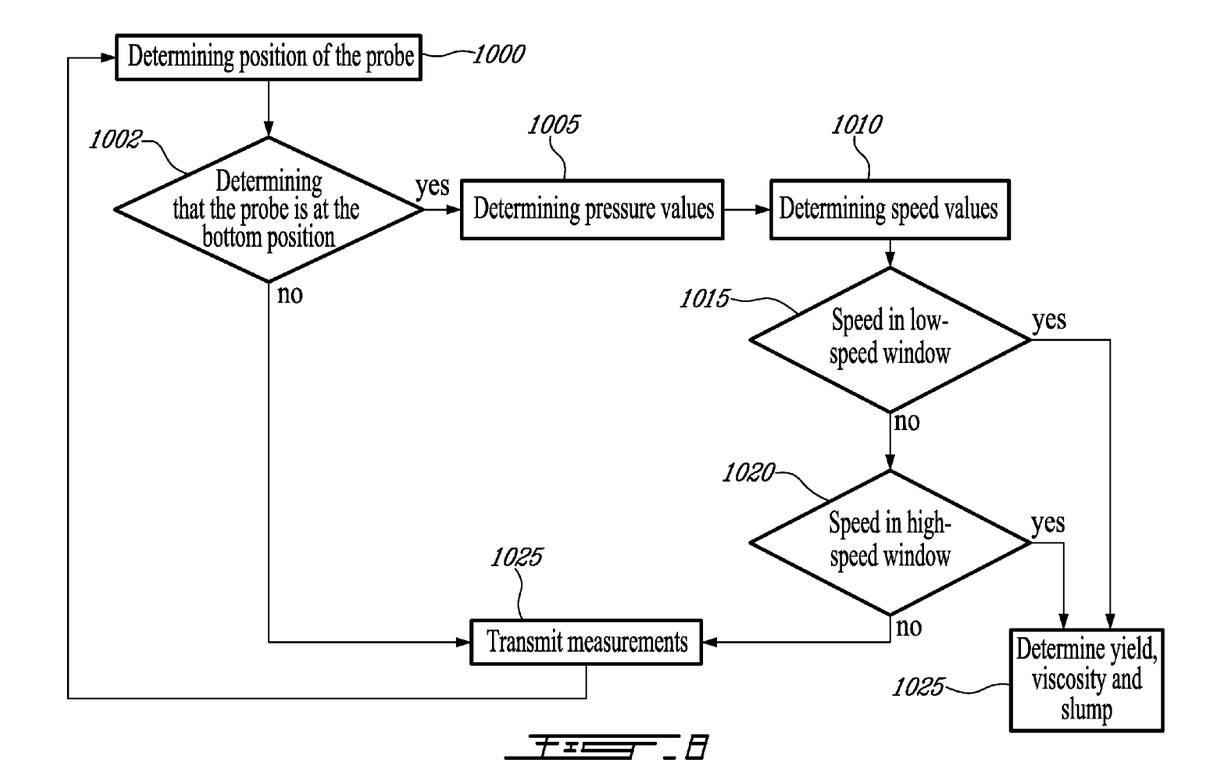
FIG. 8 is a flow chart of a method in accordance with an embodiment.

Reference is now made to FIG. 8, which is a flow chart of a method for determining properties of a fluid in the mixer 2 without having to remove a sample of fluid from the mixer 2 and analyze it externally. At step 1000, the processing unit 62 determines the position of the probe 10 using at least one position sensor or accelerometer. At step 1002, the processing unit determines that the probe 10 is at the bottom position of the mixer 2. At step 1005, the processing unit 62 determines the pressure applied to the probe 10 by the fluid. The processing unit 62 is in electronic communication with the load cell 14. The load cell detects a deformation of the outer member 13 resulting from a force applied by the fluid on the probe 10. The load cell 14 then generates an electrical variation, which is transmitted to the processing unit 62 which can interpret it to corresponding to a given pressure (or corresponding force) applied by the fluid. The load cell reading can be selectively obtained when the probe 10 is determined to be immersed inside the substance, and optionally at or near the bottommost position.

At step 1010, the processing unit 62 determines speed values of the probe 10 using the determined position from the position sensor or accelerometer. The force and pressure determined at step 1005 are thus determined at multiple ranges of speed values of the probe 10. At step 1015 the probe 10 makes measurements using a low speed window and At step 1020 the probe 10 makes measurements using a high speed window.

At step 1025, the probe 10 determines the properties of the fluid based on speed values of the probe 10, force values and pressure values when the probe 10 is in operation in the mixer 2 and at the bottom point in the mixer 2. The properties can be, for example, the viscosity and the yield of the fluid. Then a rheological curve can be determined with the viscosity and yield of the fluid. A slump can then be determined using the yield without having to remove a sample of fluid from the mixer 2 and analyze it externally. This allows the probe 10 to determine the workability of the fluid, which can be further wirelessly transmitted to the receiver 3. At step 1025, the processing unit 62 continuously transmits the last computed data to the receiver 3.

Referring back to FIG. 2, the radio transmitter 20 can broadcast measurements and readings data of the sensors to the receiver 3 at regular intervals. The measurements and readings data can be combined with a probe unique serial number to create a radio packet. The probe can use, for example, a radio carrier at 433 MHz and a On-Off Keying (OOK) modulation technique to transmit the radio packet, but it is understood that the radio frequency, transmission power, transmission rates can be adjusted to accommodate laws and regulations of different countries. The radio range can be, for example, 30 to 50 meters. The serial number in the radio packet uniquely identifies the probe from which the measurements and readings data are sent.

The receiver 3 can be any wireless receiver that can receive, store or process parameters measured with the probe 10. As will be described below, various communication standards can be used to transmit measurements and readings from the probe 10 to the receiver 3.

The receiver 3 can include power means, a radio receiver equipped with an antenna, a microcontroller having a memory and a processing unit, a display (LCD display), a RS-232 serial port. The receiver 3 also comprises a processor that processes data received from the probe 10. For each received data, the receiver 3 verifies the probe ID to identify from which probe data are received. Instead of being fixedly mounted, the receiver can be mobile such as hand held, for instance.

In one embodiment, the receiver 3 can be installed either on a truck or is installed at a batching plant. If provided on the truck, it filters the received data to keep only the data from the probe on this truck. It provided at a batching plant, it will not filter using the probe ID and will therefore monitor all the probes that are in radio range. On a typical receiver 3, the raw sensor readings such as the speed of a mixer, a pressure applied on a probe, and a temperature are displayed in the screen for information purposes.

The last rheological test results and workability information (viscosity, yield and slump) can also be displayed. Although the probe can monitor the speed of the mixer 2 to automatically perform a two-point test, if the truck operator never sets the speed in one of the speed window, the rheological curve will not be updated. The display can also indicate if the rheological curve is too old and guide the operator to activate the mixer at a target speed and re-acquire the missing point.

In one embodiment, data can be sent to an output data port (such as RS-232 serial port) which can be used by advanced logging systems (truck or plant monitoring systems) to combine the probe readings with other truck/plant operation readings for instance.

In the illustrated example however, no further processing is undertaken by the receiver 3 and the probe has already computed all the calculations. However, nothing prevents the implementation of other workability parameters computation algorithms using the raw data from the sensors. For example, instead of a two-point rheological test, a multiple-point rheological test can be made, or different slump models can be implemented. The probe can also be used for truck fleet management purposes. The mixer rotation direction is a direct indication as to whether the truck is mixing the fluid slowly (transit), fast (mix before delivery), or in reverse direction (emptying the mixer, for example in a concrete mixer truck embodiment).

In a system having a plurality of probes, which are used in a close range scenario on the same or separate mixer units, a radio receiver can distinguish from which probe the measurements and readings data are sent from using that serial number. Alternatively, any other unique identification number can be used instead of the serial number. Besides OOK, other modulation techniques can be used such frequency modulation (FM), phase modulation (PSK) and narrow band modulations such as gaussian frequency/phase shift keying (GFSK/ GPSK). Complete standardized radio systems such as Bluetooth and ZigBee could also be used. Other wireless standards could be used, such as infrared transmission and acoustical (ultrasound) data transmission.

In one embodiment, the processing unit 62 can transmit different types of measurements such as the speed and the direction of rotation of the mixer 2 to the receiver 3. The measurements can be sent in a radio data packet identified with an identification number of the probe 10. Therefore, each time the receiver 3 receives a radio data packet from a same probe it may increment a sequential number incremented for each radio transmission. Then the receiver 3 can determine, a last read temperature, the last read speed of the mixer, The last read point (pressure, speed, age), the last known low-speed point (pressure, speed, age), the last known high-speed point (pressure, speed, age), the last computed workability parameters (yield, viscosity, slump, age), and a checksum or CRC (cyclical redundancy check) for data integrity. The age refers to a period in time and the number of times a measurement was made. The receiver 3 can use the information for example, as a timestamp to inform a user of an age of measurements, which can be too old or not valid anymore depending on a certain threshold.

The speed direction can determine whether the mixer 2 is empty. The mixer 2 can be determined to be empty when, for example, a number of revolutions have been made by the mixer 2 at high or constant speed in a certain unloading direction. Alternatively, the mixer can be determined to be empty when the force sensor does not detect resistance by the fluid.

The rotation direction of the mixer 2 can be used when loading the mixer 2, for example, at a batching plant. When the rotation direction is adequate, a batching plant operator can safely load the concrete into the mixer without spillage of concrete. Alternatively, the readings from the probe 10 can also be used directly by the batching plant operator (or software) to set a condition to start loading the concrete into the mixer 2.

Those skilled in the art will understand that the probe 10 is not necessarily limited to the number of elements shown in FIGS. 3 and 4. For example, the probe 10 may comprise more load cells or sensors. More particularly, it should also be understood that FIGS. 3 and 4 depict simplified hardware and software parts, and that other hardware and software parts may have been omitted for clarity reasons. Those skilled in the art will understand that the hardware parts of the probe 10 include processors and electronic parts to execute the method described above. Those skilled in the art will understand that the software parts of the probe 10 include instructions and computer code that are executed by the processors and electronic parts to process the measurements and readings made by the probe 10, to determine properties for the fluid and to transmit data to a receiver.

Figure 9:
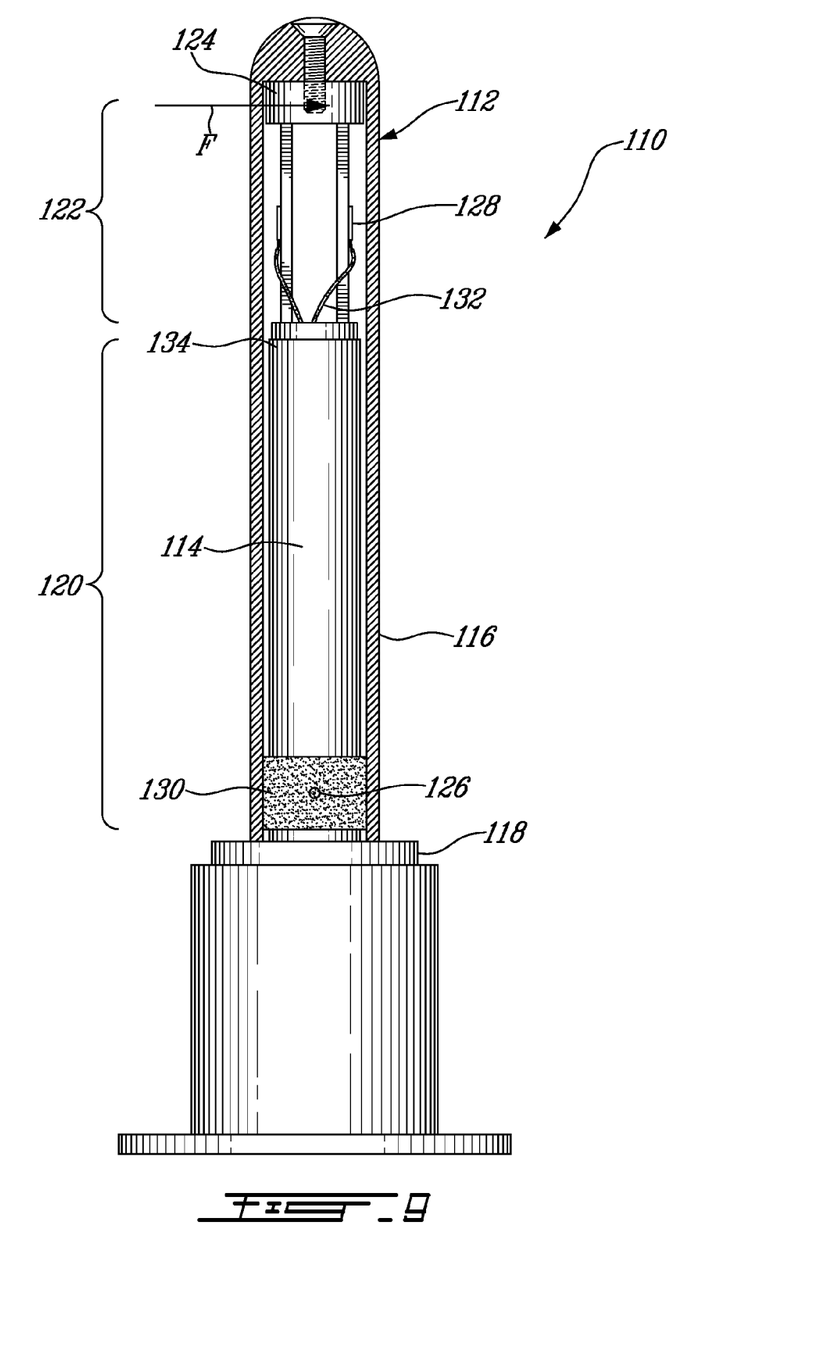
FIG. 9 is a side view, partly sectioned, of another example of a probe.

Turning now to FIG. 9, another embodiment of a probe 110 is shown. In this embodiment the resistance member 112 also includes an inner member 114 and an outer member 116 (or shell). The inner member 114 is fixed to and extends away from the base 118. It can be said to have successively a base portion 120 adjacent the base 118, a deformation portion 122, and a tip 124. The shell 116 entirely covers the inner member 114 and collectively with the base 118, prevents intrusion of the substance to characterize. It can be pivotally mounted near the base, and fixedly connected at the tip 124, to allow transmission of a force F caused by the frictional resistance or pressure of the substance along the length of the shell (as the probe is immersed and is being displaced relative to it) onto the inner member 114 in a manner to deform the deformation portion 122. The deformation portion 122 can have a strain gauge to obtain an indication of the deformation of the deformation portion 122 and thus an indication of the force F. In this example, the pivoting is achieved by mounting the lower end of the shell 116 in a tight fit manner around an annular bushing 130 provided around the base portion 120 of the inner member 144 rather than by using a pivot shaft for instance. This can be advantageous in providing a more direct reading which can be lost in cases where a loose pivot shaft is used given the size of the deformations envisaged here. The pivot axis 126 of the shell can thus be said to go across the inner member 114 and bushing 130 in this case.

In this particular example, the deformation sensor can have a load cell including one or more strain gauges for instance. Using two strain gauges on opposite sides can potentially allow better reading the resistance force in both directions and even determining the rotation direction of the drum otherwise than by the use of an extra accelerometer. The strain gauge 128 is provided on a flat, relatively easy to deform portion of the inner member 114 to optimize measurements given the capacity of the strain gauge 128. The wire 132 connecting the strain gauge to an electronic module can pass through a hollow in the inner member 114, for instance. The deformation portion 122 can thus be specifically designed to offer elastic deformation up to a predetermined maximum reading value. In this specific example, the deformation portion is machined into a hollow steel pipe to form two parallel flat metal portions.

To protect the deformation portion 122 from going into the plastic deformation range if ever the maximum estimated force is exceeded, the inner member 114 can be provided with an abutment portion 134 below the deformation portion 122, which abuttingly receives the shell 116 in the event the maximum deformation is reached, and prevents transmission of further force, to prevent further deformation.

Alternately to a deformation sensor, for instance, it will be understood that a pressure sensor can be used between the inner member and shell to achieve a comparable result, for instance.

Figure 10:
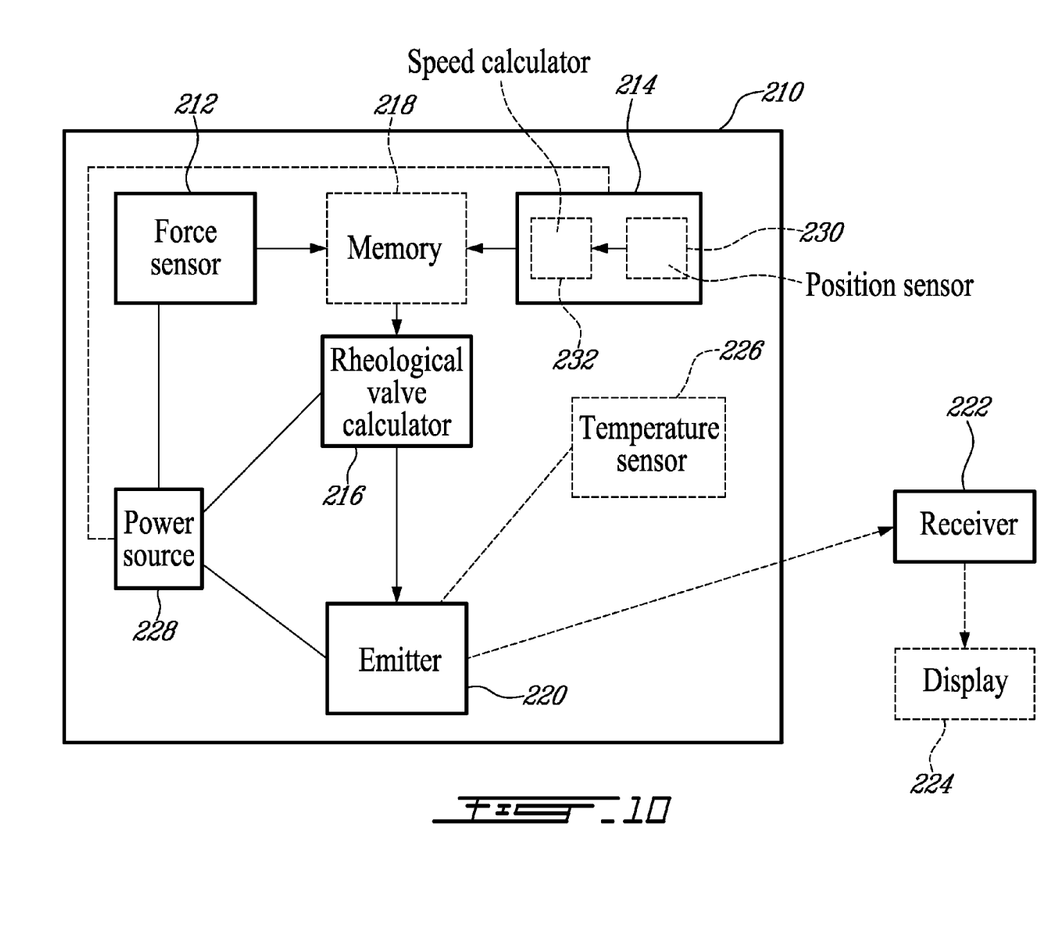
FIG. 10 is a block diagram representation of another example of a probe.

Turning now to FIG. 10, an alternate embodiment of a probe 210 is shown. In this case, the probe has a force sensor 212 (or pressure sensor) to obtain a value indicative of the pressure exerted by the substance on the resistance member, and a speed sensor 214 to obtain a value indicative of the speed of displacement of the probe 210 relative the substance. A rheological value calculator 216 can be used to determine a value indicative of at least one rheological property of the substance based on the force value and the speed value for instance. To obtain values indicative of yield and viscosity, for instance, the rheological value calculator can use at least one force value and speed value combination corresponding to a moment in time in a low speed range, and at least one force value and speed value combination corresponding to a moment in time in a high speed range. To this end, these values can be stored in a memory 218 for use by the rheological value calculator 216. The rheological value(s) can be transferred along to an emitter 220, which can transmit data wirelessly to a receiver 222 for instance, which can be connected to a display 224 for instance.

The speed sensor can be any suitable speed sensor. One example can include a position sensor 230 such as an accelerometer for instance, connected to a speed calculator 232 which calculates the speed based on the variation of position over time, to provide one example. In an alternate embodiment, the speed calculation and the rheological value calculation can be done by a single processing unit.

The probe 210 can further include a temperature sensor 226 for instance or one or more other sensors. The data from the temperature sensor 226 can also be emitted by the emitter 220. The probe will typically include a power source 228 which can provide power to any module which requires power in the probe.

In an alternate embodiment, the emitter can be omitted and the data can be obtained directly from a port or an indicator which can be provided in the base of the probe for instance, or the emitter can be a wired emitter instead of a wireless emitter for instance. In another alternate embodiment, the rheological value calculator can be provided externally to the probe, and the emitter can transmit primary data such as force data, speed data, or position data for instance.

The embodiments described above are intended to be exemplary only. The scope of the invention is therefore intended to be limited solely by the scope of the appended claims.

The invention claimed is:

1. A rheological probe for use in obtaining at least one value indicative of a rheological property of a substance in which the rheological probe is to be immersed and relative to which the rheological probe is to be transversally moved, the rheological probe comprising:
    a base
    an inner member fixedly connected to the base and extending away therefrom, the inner member having in succession a base portion proximate the base, a deformation portion located away from the base, and a tip;
    a shell member covering the inner member from the tip and downwardly along the deformation portion and base portion, the shell member being pivotable about an axis extending through and across the base portion when subjected to a resistance pressure imparted by the relative movement in the rheological substance, and being connected to the tip to transfer a force resulting from the resistance pressure and thereby elastically deform the deformation portion; and
    a deformation sensor mounted to the deformation portion for providing a value indicative of the resistance pressure.

2. The rheological probe of claim 1, further comprising an abutment between the deformation portion and the base portion of the inner member, said abutment transversally projecting from said deformation portion to the extent of coming into abutment with the shell member and stopping pivoting thereof prior to said deformation portion reaching a predetermined maximum elastic deformation.

3. The rheological probe of claim 2 wherein said maximum elastic deformation is in the order of the millimeter.

4. The rheological probe of claim 1 wherein the shell member is pivotable by abutting contact against a resilient bushing positioned around the base portion of said inner member.

5. The rheological probe of claim 1 wherein said inner member is in the shape of an elongated stem with a lower half and an upper half, said deformation portion being said upper half.

6. The rheological probe of claim 5 wherein both the lower half and the upper half have a length in the order of the decimeter.

7. The rheological probe of claim 1 wherein the deformation sensor includes at least one load cell.

8. The rheological probe of claim 7 wherein the base is hollow and includes an electronic module, and the inner member is hollow, further comprising an electrical connection passing through the hollow inner member and connecting the load cell to the electronic module.

9. A rheological probe for use in obtaining at least one value indicative of a rheological property of a substance in which the rheological probe is to be immersed and relative to which the rheological probe is to be transversally moved, the rheological probe comprising:
- a base;
- an inner member fixedly connected to the base and extending away therefrom, the inner member having in succession a base portion proximate the base, a deformation portion located away from the base, and a tip;
- a shell member covering the inner member from the tip and downwardly along the deformation portion and base portion, the shell member being pivotable about an axis extending across the base portion when subjected to a resistance pressure imparted by the relative movement in the rheological substance, and being connected to the tip to transfer a force resulting from the resistance pressure and thereby elastically deform the deformation portion;
- a deformation sensor mounted to the deformation portion for providing a value indicative of the resistance pressure; and
- an abutment between the deformation portion and the base portion of the inner member, said abutment transversally projecting from said deformation portion to the extent of coming into abutment with the shell member and stopping pivoting thereof prior to said deformation portion reaching a predetermined maximum elastic deformation.

* * * * *